US00PP26544P3

(12) United States Plant Patent
Tristram

(10) Patent No.: US PP26,544 P3
(45) Date of Patent: Mar. 29, 2016

(54) ***RHODODENDRON* PLANT NAMED 'WALPINRUF'**

(50) Latin Name: ***Rhododendron kaempferi* hybrid**
Varietal Denomination: WALPINRUF

(71) Applicant: David Tristram, Arundel (GB)

(72) Inventor: David Tristram, Arundel (GB)

( * ) Notice: Subject to any disclaimer, the term of this patent is extended or adjusted under 35 U.S.C. 154(b) by 112 days.

(21) Appl. No.: 14/120,663

(22) Filed: Jun. 13, 2014

(65) Prior Publication Data

US 2014/0380537 P1 Dec. 25, 2014

Related U.S. Application Data

(60) Provisional application No. 61/956,956, filed on Jun. 20, 2013.

(51) Int. Cl.
*A01H 5/00* (2006.01)
*A01H 5/02* (2006.01)

(52) U.S. Cl.
USPC ..... Plt./239
CPC ..... *A01H 5/02* (2013.01)

(58) Field of Classification Search
USPC ..... Plt./239
See application file for complete search history.

*Primary Examiner* — Annette Para
(74) *Attorney, Agent, or Firm* — James M. Weatherly; Bethany R. Roahrig; Cochran Freund & Young, LLC

(57) ABSTRACT

A new and distinct variety of *Rhododendron* plant named 'WALPINRUF' which is characterized by a compact mounding habit, glossy evergreen foliage, large double flowers in a warm pink color, which are produced from spring until early summer, is disclosed.

2 Drawing Sheets

Genus and species: *Rhododendron kaempferi* hybrid.
Variety denomination: 'WALPINRUF'.

BACKGROUND OF THE NEW PLANT

The present invention relates to a new and distinct cultivar of *Rhododendron*, also commonly known as evergreen azalea, which is grown as an ornamental shrub for use in planted containers and in the garden and landscape. The new cultivar is known botanically as *Rhododendron kaempferi* hybrid, and will be referred to hereinafter by the cultivar name 'WALPINRUF'.

'WALPINRUF' arose and was selected from a long term breeding program commenced in 1993 or 1994. The aim of the breeding program was to develop one or more matched series of novel cultivars of hardy evergreen azaleas with showy flowers. Breeding commenced with Azalea 'Elsie Lee' as one of the initial parents. Azalea 'Elsie Lee' is a Shammarello hybrid, raised in Ohio in the 1960s and renowned for its relative hardiness among evergreen azaleas. Although several Shammarello hybrids were patented in the 1960s and 1970s, Azalea 'Elsie Lee' is believed to be unpatented. 'Elise Lee' bears light mauve-blue semi-double flowers.

Commencing in 1993 or 1994, many generations of deliberate hybrids were raised, selecting promising parents from previous unnamed seedlings which had been raised during the breeding program. 'WALPINRUF' was selected in 2003 or 2004. The parents of 'WALPINRUF' are unknown and have not been retained: no parental comparison information is available.

Asexual propagation of 'WALPINRUF' was first accomplished in 2003 or 2004 using semi-ripe shoot cuttings. Since that time, under careful observation, the distinguishing characteristics of 'WALPINRUF' have been determined stable and uniform, and to reproduce true to type in successive generations of asexual propagation.

SUMMARY

The distinguishing characteristics of 'WALPINRUF' are as follows: 'WALPINRUF' has not been tested under all possible conditions and phenotypic differences may be observed with variations in environmental, climatic, and cultural conditions.

1. Plants of 'WALPINRUF' exhibit a compact mounding growth habit.
2. The foliage of 'WALPINRUF' is glossy evergreen in color.
3. 'WALPINRUF' bears large double flowers in a warm pink color.
4. Plants of 'WALPINRUF' show good heat and humidity tolerance.
5. 'WALPINRUF' blooms from late spring through early summer.
6. After two years of growth, plants of 'WALPINRUF' are 25 cm to 30 cm in height and 25 cm to 30 cm in width.
7. At maturity, 5 years, plants of 'WALPINRUF' are 30 cm to 40 cm in height and 30 cm to 40 cm in width.
8. 'WALPINRUF' prefers semi-shade in a moist, well drained, slightly acidic growing media.
9. 'WALPINRUF' is suitable for use as a garden specimen, landscape plants and as a container specimen.
10. 'WALPINRUF' is hardy to at least USDA Zone 7.

COMPARISON WITH KNOWN VARIETIES

'WALPINRUF' may be compared with the following two varieties of azalea: Azalea 'Roblec' (U.S. Plant Pat. No. 15,339) and Azalea 'Roblea' (U.S. Plant Pat. No. 12,142). Whereas 'WALPINRUF', 'Roblec' and 'Roblea' all bear semi-double pink flowers, the comparison varieties 'Roblec' and 'Roblea' were developed and selected for their ability to rebloom in late summer and fall. 'WALPINRUF' blooms only in the late spring through early summer and does not rebloom.

'WALPINRUF' may also be compared with Azalea 'YBAZ-2504' (U.S. Plant Pat. No. 21,475). Whereas 'WALPINRUF' and 'YBAZ-2504' bear semi-double pink flowers, the comparison variety 'YBAZ-2504' is a florist or greenhouse variety which is not hardy. 'WALPINRUF' has been observed to tolerate temperatures as low as −15° C. (USDA Hardiness Zone 7).

DESCRIPTION OF THE PHOTOGRAPHS

The accompanying color photographs illustrate the overall appearance of 'WALPINRUF' showing the colors of its foliage and flowers as true as it is reasonably possible to obtain in colored reproductions of this type. Both photographs have been made from two year old plants which have been grown out of doors in Sacramento, Calif.

BOTANICAL DESCRIPTION OF THE PLANT

Figure 1:
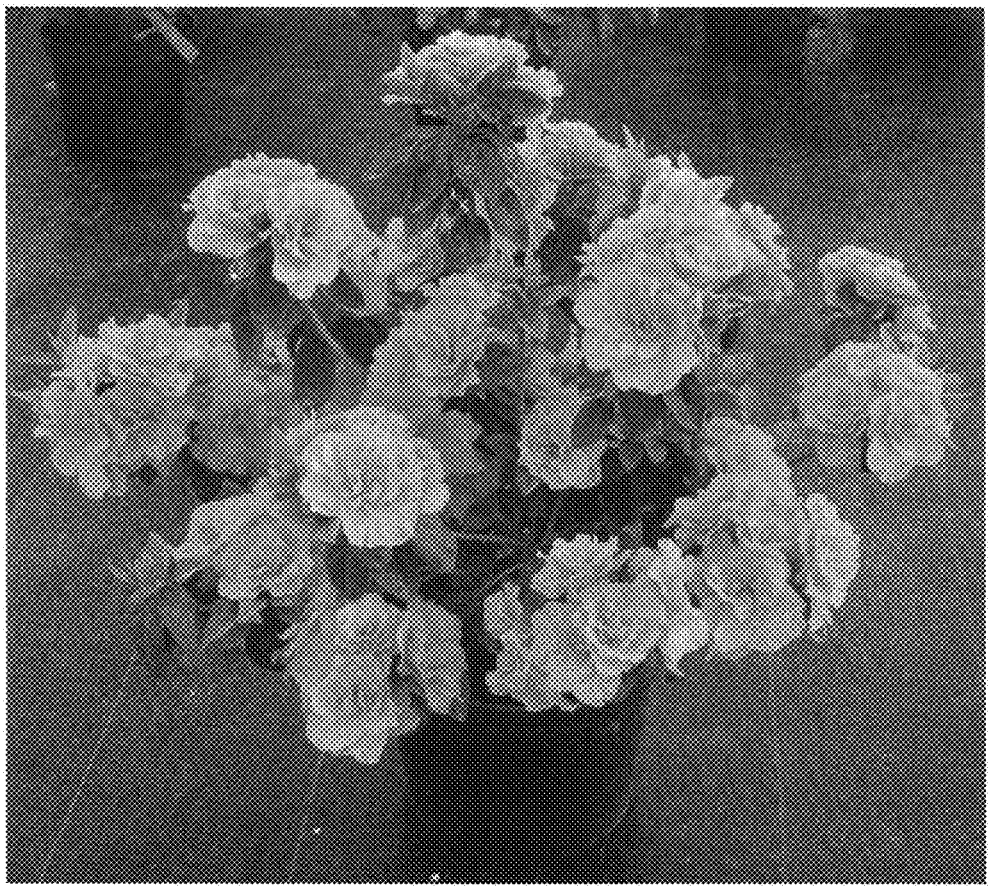
FIG. 1 shows an entire or whole plant of 'WALPINRUF'.
Figure 2:
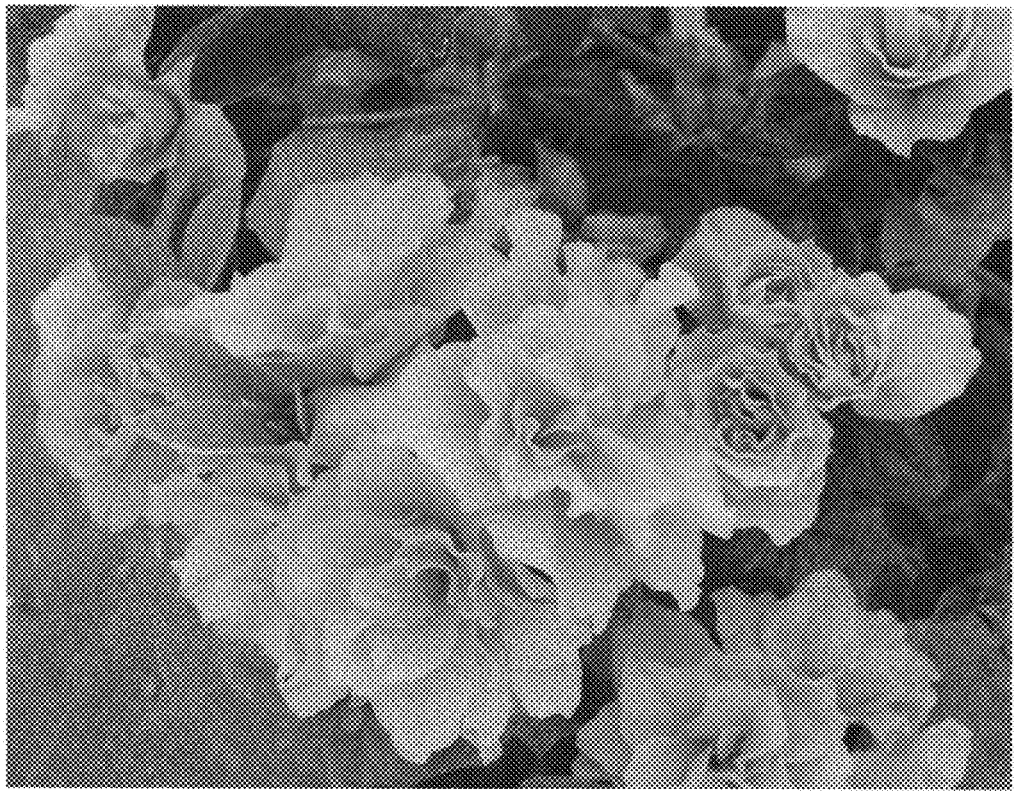
FIG. 2 depicts a close-up view of the flowers of 'WALPINRUF'.

The following is a detailed description of 'WALPINRUF'. The observed plant was 2 years old growing outdoors in a 1-gallon container in Santa Barbara, Calif. Observations, measurements, values and comparisons were collected in April of 2014 where the botanical description was made. The color determinations are in accordance with the 2007 edition of The Colour Chart of The Royal Horticultural Society, London, England, except where general color terms of ordinary dictionary significance are used. Growing conditions are similar to those of other *Rhododendron.*

Botanical classification:
- *Genus.*—*Rhododendron.*
- *Species.*—*kaempferi* hybrid.
- *Cultivar.*—'WALPINRUF'.
- *Commercial classification.*—Perennial.
- *Common name.*—Evergreen Azalea.

Parentage: Unnamed seedlings raised during the breeding program. Parents not retained or described.

Propagation method: Semi-ripe cuttings without use of rooting hormone.

Plant description:
- *Use.*—Ornamental for container or landscape.
- *Cultural requirements.*—Plant in partial shade and any free-draining slightly acidic soil.
- *Particular pest resistance or susceptibility.*—None observed.
- *Rooting system.*—Fine and fibrous.
- *Vigor.*—Moderately vigorous. Lateral branching is encouraged by pinching.
- *Habit.*—Inverted cone.
- *Dimensions after two years.*—25 cm to 30 cm in height and 25 cm to 30 cm in width.
- *Dimensions after five years.*—30 cm to 40 cm in height and 30 cm to 40 cm in width.
- *Hardiness.*—USDA Zone 7.

Stem:
- *Dimensions.*—Length 1.5 cm (height of manual pinch). Diameter at base: 1 cm.
- *Shape.*—Cylindrical.
- *Bark.*—Rough, color 172A.
- *Number of branches.*—12.

Branches (current season extension growth):
- *Shape.*—Cylindrical.
- *Dimensions.*—Length: 18 cm to 25 cm, diameter 3 mm to 4 mm.
- *Color.*—N144A.
- *Internode length* (*range*).—1 cm to 2 cm.

Branches (previous year's growth):
- *Shape.*—Cylindrical.
- *Dimensions.*—Length: 20 cm to 25 cm, diameter 3 mm to 4 mm.
- *Color.*—172A.
- *Bark surface.*—Rough.
- *Internode length* (*range*).—1 cm to 2 cm.

Foliage:
- *Type.*—Evergreen.
- *Leaf arrangement.*—Alternate.
- *Leaf division.*—Simple.
- *Leaf dimensions* (*average, fully developed*).—5 cm in length and 3 cm in width.
- *Leaf color* (*current season new growth, adaxial surface*).—144A.
- *Leaf color* (*current season new growth, abaxial surface*).—144A.
- *Leaf color* (*mature, previous year's growth, adaxial surface*).—147A.
- *Leaf color* (*mature, previous year's growth, abaxial surface*).—138A.
- *Leaf shape.*—Elliptic, base cuneate, apex obtuse.
- *Leaf margin.*—Ciliate, hairs fine, 1 mm to 2 mm, silver-gray 156D.
- *Leaf surface* (*both surfaces*).—Smooth, glossy, pubescent, hairs fine, 1 mm to 2 mm, silver-gray 156D.
- *Venation.*—Pinnate, color 144A.
- *Petioles.*—Dimensions: 5 mm in length, 1.5 mm in width. Color: N144A.

Inflorescence:
- *Inflorescence type.*—Terminal.
- *Flower arrangement.*—Flowers in groups of 8 to 10.
- *Flower aspect.*—Upward or outward.
- *Form.*—Rotate.
- *Inflorescence quantity.*—Ranges between 3 and 5 per branch and between 30 and 50 at peak of flowering.
- *Dimensions of inflorescence* (*average*).—10 cm in diameter, 8 cm in depth.
- *Blooming season.*—Spring.
- *Lastingness of flowers* (*on the plant*).—7 to 10 days.

Bud:
- *Arrangement.*—Borne in clusters of 8 to 10 buds. Initially, each bud is sheathed by a pair of modified leaf bracts which fall away as the bud swells.
- *Bud shape.*—Ovoid.
- *Dimensions* (*immediately prior to opening*).—18 mm in length and 12 mm in diameter.
- *Bracts* (*bud sheath*).—Pair, each 15 mm in length and 10 mm in width.
- *Bracts* (*bud sheath*).—Shape cupped, texture paper-like, base truncate, apex acute.
- *Bract color* (*both surfaces*).—167C.
- *Bud color* (*as bracts fall away, as bud opens*).—39B.
- *Sepals.*—5 in number, fused at base.
- *Sepal color* (*adaxial surface*).—191B, surface pubescent, hairs fine, 1 to 2 mm, silver-gray 156D.
- *Sepal color* (*abaxial surface*).—137B, surface smooth.
- *Sepal dimensions.*—Length: 8 mm; width: 6 mm.

*Sepal shape*.—Ovate, base rounded, apex cuspidate.

*Sepal surface*.—Pubescent, many fine hairs 1 mm to 2 mm, silver-gray 156D.

*Pedicel*.—Length 18 mm, width 1.5 mm.

*Pedicel surface*.—Pubescent, many fine hairs 1 mm to 2 mm, color 191B.

Flowers (petals and petaloids):

*Form*.—Semi-double.

*Flower dimensions*.—6 cm in diameter, 2.5 cm to 3.0 cm in depth.

*Petal arrangement*.—Three whorls, each whorl consisting of 5 petals fused at base.

*Petal shape*.—Widely ovate, base truncate, apex rounded.

*Petal dimensions*.—Outer whorl: 35 mm in length, 30 mm in width. Second whorl: 32 mm in length, 25 mm in width. Inner whorl: 26 mm in length, 22 mm in width.

*Petal margin*.—Smooth, gently ruffled.

*Petaloids*.—Occasionally present, approximately 2 to 3 per flower. Shape: Subulate, irregular. Dimensions: 12 mm in length, 2 mm to 7 mm in width.

*Petals and petaloids*.—Color (both surfaces): Opening N66B becoming N66C when fully developed. Spots: Occasionally present as short dashes towards petal base, length 1 mm to 2 mm, width 0.5 mm to 1.0 mm, color red-purple 61B. Surface: Smooth, glossy.

*Venation*.—Parallel, color N66B.

*Peduncle*.—Dimensions: 5 mm in length, 2 mm in width, ribbed. Surface: Smooth. Color: 144D.

Reproductive organs:

*Stamens, anthers*.—Absent.

*Pistil*.—Length 5 mm, diameter 0.5 mm, color 13C.

*Stigma*.—Color 137B.

*Ovary*.—Ovate, 4 mm in length, 3 mm in diameter. Surrounded by dense very fine silver-gray hairs, nearest 156D.

I claim:

1. A new and distinct cultivar of *Rhododendron* plant named 'WALPINRUF' as described and illustrated herein.

* * * * *